(12) United States Patent
Lauer

(10) Patent No.: US 10,518,019 B2
(45) Date of Patent: Dec. 31, 2019

(54) BLOOD TREATMENT CASSETTE WITH FILM VALVE AND INELASTICAL SPACER AS WELL AS BLOOD TREATMENT APPARATUS

(71) Applicant: FRESENIUS MEDICAL CARE DEUTSCHLAND GMBH, Bad Homburg (DE)

(72) Inventor: Martin Lauer, St. Wendel (DE)

(73) Assignee: Fresenius Medical Care Deutschland GmbH, Bad Homburg (DE)

( * ) Notice: Subject to any disclaimer, the term of this patent is extended or adjusted under 35 U.S.C. 154(b) by 432 days.

(21) Appl. No.: 15/126,251

(22) PCT Filed: Mar. 13, 2015

(86) PCT No.: PCT/EP2015/055295
§ 371 (c)(1),
(2) Date: Sep. 14, 2016

(87) PCT Pub. No.: WO2015/136074
PCT Pub. Date: Sep. 17, 2015

(65) Prior Publication Data
US 2017/0136169 A1    May 18, 2017

(30) Foreign Application Priority Data
Mar. 14, 2014    (DE) .......................... 10 2014 103 491

(51) Int. Cl.
*A61M 1/36*    (2006.01)

(52) U.S. Cl.
CPC .......... *A61M 1/367* (2013.01); *A61M 1/3639* (2013.01); *A61M 2205/128* (2013.01); *A61M 2206/20* (2013.01)

(58) Field of Classification Search
CPC ...... A61M 1/14; A61M 1/168; A61M 1/3639; A61M 1/367; A61M 2205/128; A61M 2206/20
See application file for complete search history.

(56) References Cited

U.S. PATENT DOCUMENTS

2008/0077068 A1    3/2008    Orr
2009/0215602 A1    8/2009    Min et al.
(Continued)

FOREIGN PATENT DOCUMENTS

CN    102497895    6/2012
DE    102009012632    9/2010
(Continued)

OTHER PUBLICATIONS

International Search Report from PCT/EP2015/055295, dated May 20, 2015.

*Primary Examiner* — Benjamin J Klein
(74) *Attorney, Agent, or Firm* — Fish & Richardson P.C.

(57) ABSTRACT

A blood treatment cassette having a cassette body, designed as a hard part, and a film, wherein the film is connected with the hard part and covers the hard part at least partially, wherein the hard part comprises at least one valve base of a valve and wherein the valve is embodied to take, in addition to a first, open position of the valve in which the valve base and the section of the film that is arranged above it do not touch each other, a second, closed position of the valve when applying force on the section of the film in which the valve base and the section of the film touch each other.

16 Claims, 7 Drawing Sheets

(56) References Cited

U.S. PATENT DOCUMENTS

2011/0015610 A1    1/2011    Plahey et al.
2012/0080437 A1    4/2012    Guenther et al.
2013/0331774 A1   12/2013   Farrell et al.

FOREIGN PATENT DOCUMENTS

| WO | 2010-121819 A1 | 10/2010 | | |
|---|---|---|---|---|
| WO | WO 2010/121740 | 10/2010 | | |
| WO | 2014-035471 A1 | 3/2014 | | |
| WO | WO-2014035471 A1 | * | 3/2014 | .............. A61M 1/14 |

* cited by examiner

BLOOD TREATMENT CASSETTE WITH FILM VALVE AND INELASTICAL SPACER AS WELL AS BLOOD TREATMENT APPARATUS

CROSS REFERENCE TO RELATED APPLICATIONS

The present application is the national stage entry of International Patent Application No. PCT/EP2015/055295, filed on Mar. 13, 2015, and claims priority to Application No. DE 10 2014 103 491.0, filed in the Federal Republic of Germany on Mar. 14, 2014, the disclosures of which are expressly incorporated herein in their entirety by reference thereto.

TECHNICAL FIELD

The present invention relates to a blood treatment cassette and a blood treatment apparatus.

BACKGROUND

Single-use systems are being increasingly realized in the medical or laboratory technology as compact medical functional devices such as cassette systems or blood treatment cassettes in which liquids and gases, in particular medical fluids and blood, are conducted in channels and chambers. If they are provided for a single use, one speaks of disposable cassettes or single-use cassettes.

In most cases, these are hard-part film cassettes. The hard part regularly consists of an injection molding material such as PE, PP, PA, ABS, PMMA, PC or PVC. In it, for example, hose connections, connectors, chambers, channels and alignment devices are embodied. The chambers and channels are usually designed as semi-open, fluid-conducting structures. A film made of material compatible to the hard part (suitable for welding or gluing to the hard part) seals the semi-open structures and completes them to fully adequate chambers and channels. The film may only be, for example, welded on or glued to the blood treatment cassette at an outer or closed or peripheral edge. There also are designs where the boundaries of the chambers and channels, the so-called channel edge bars, are welded on or glued to the film in strip form or over a larger area. In this manner, blood treatment cassettes which already provide a defined fluid conduction, prior to being equipped in a treatment machine and after being removed, are produced.

Certain areas of the hard part and the film are often deliberately not welded on or glued to each other. These areas may be used as film valves between different fluid conducting areas. For this purpose, the blood treatment cassette is inserted in the blood treatment apparatus between a door and an actuator-sensor-unit of the blood treatment apparatus, and subsequently by closing the door, the latter is brought into a so-called grouting or pressing position in which the film is grouted or pressed against the hard part, and the blood treatment cassette with the film is coupled in a spatially defined manner to the actuator-sensor mat of the actuator-sensor unit. Actuators integrated into the actuator-sensor mat and actuator-sensor plate (or unit) may be able to exercise movements through or over the film, by which, for example, pump or valve functions may be realized. Properties of fluids which flow through the blood treatment cassette may be measured by means of at least one sensor optionally provided on the actuator-sensor-plate.

Production or processing problems may, however, occur particularly with blood treatment cassettes in which the films and film valves are welded such that they are flush with the channel edge along the latter.

SUMMARY

Aspects of the present invention relate to blood treatment cassettes and blood treatment apparatuses with which the blood treatment cassettes are used.

In one aspect, a blood treatment cassette has a cassette body, designed as hard part, and a film. The film is connected to the hard part, e.g. through welding or gluing, and the hard part is at least partially covered by the film against the outside to form channels and chambers or parts thereof. Furthermore, the hard part comprises at least one valve seat or section of a valve, herein also denoted as valve base of the valve.

The valve is designed to take a first position and a second position, or valve position, which is different from the first one. Thereby, the first position is a position in which the valve is open, in particular for the gas sterilization of sections of the hard part. In the first position, the valve base and a section of the film, which during the use of the treatment cassette is or will be positioned above the valve base, do not touch each other. The valve is configured and provided such that it moves or transitions into the second closed position in case a force is applied, in particular a force directed towards the valve base and acting on the section of the film on top of the valve base. In the second position, the valve base and the section of the film touch each other, for example directly or indirectly. In the second position, the valve is closed.

In addition, the hard part and the film touch each other in a main contact plane, and are connected to each other in the main contact plane along channel bars that extend alongside chambers or channels of the hard part. The blood treatment cassette comprises in the area of the valve at least one hump supported by the hard part and/or integrally produced therewith. Thereby, the hump is arranged in such a way to ensure or support sustaining the valve in the first, open position when the blood treatment cassette is in a no-load or un-grouted non-use condition.

Further, a blood treatment apparatus is proposed which can be connected with a blood treatment cassette and comprises an actuator-sensor-plate with at least one actuator. The latter is intended for the interaction between actuators and/or sensors of the blood treatment apparatus with devices of the blood treatment cassette.

In all of the following embodiments, the use of the expressions "may be" or "may have" etc., is to be understood synonymously with "preferably is" or "preferably has", respectively, and so on, and is intended to illustrate exemplary embodiments.

Whenever a numerical word is mentioned herein, the skilled person understands this as an indication of a numerical lower limit. Provided it does not lead to any contradiction discernible for the skilled person, the skilled person in these cases implicitly understands for example "one" always as "at least one". This understanding is also encompassed by the present invention as well as the interpretation that a numeric word, for example, "one" can alternatively be meant as "exactly one", wherever this is technically possible in the view of the skilled person. Both are encompassed by the present invention and apply to all used numerical words herein.

The herein given spatial information such as "top", "bottom", etc. refer, in case of doubt, to the illustrations shown in the here enclosed figures.

Embodiments may comprise one or more of the following features in any arbitrary combination.

In specific exemplary embodiments, the valve is designed to be transferable or to be transferred from the first position into the second position by pressure applied on the valve by an actuator of a blood treatment apparatus, for the operation of which the blood treatment cassette is appropriately connected with the blood treatment apparatus.

In certain exemplary embodiments, the valve is designed as a film or a phantom valve.

In some particular exemplary embodiments, the hump projects over the main contact plane away from the hard part.

In some exemplary embodiments, the hump projects above the valve base by 2 to 4 times the thickness of the film.

In specific exemplary embodiments, there is an internal space which is 6 to 12 times the thickness of the film between the valve base and the next adjacent section of the hump in a plane parallel to the main extension plane of the film.

In certain exemplary embodiments, a section of the hump, preferably the hump front area, i.e. the section with which the hump comes into contact with the film or may come into contact therewith, comprises a diameter. This diameter is 5 to 12 times the thickness of the film.

In some particular exemplary embodiments, the hump is not a section of the channel bars which edge or boarder chambers or channels.

The hump, in certain exemplary embodiments, is at the best case arranged in a channel or chamber. It is however not a part of the flow-conducting edge of channel or chamber.

In some exemplary embodiments, a space is intended to be between the hump and the adjacent channel bars. It corresponds to 3 to 8 times the diameter of the hump, in particular in the area in which the hump touches the film.

In specific exemplary embodiments, the valve base is arranged at the level of the main extension plane of the film.

In certain exemplary embodiments, the valve base is designed to be flat in longitudinal direction thereof, i.e. not winding or concave or convex.

In some particular exemplary embodiments, the valve base is designed to be winding or concave or convex in longitudinal direction thereof.

In some exemplary embodiments, a dent depth (T) is 2 to 4 times the thickness of the film.

In specific exemplary embodiments, the valve base comprises a length which corresponds to 10 to 30 times the thickness of the film.

In certain exemplary embodiments, the dent depth of the valve base corresponds to 1 to 3 times the thickness of the film. Alternatively, the valve base may be reset behind adjacent channel edge bars towards the interior of the blood treatment cassette by 1 to 3 times the thickness of the film.

In some particular exemplary embodiments, the actuator-sensor-plate comprises an actuator-sensor-mat which is in contact with blood treatment cassette directly or indirectly. Thereby, the actuator-sensor-mat is in a section, which is in contact with the hump of the blood treatment cassette, thinner than the adjacent sections of the actuator-sensor-mat. In the thinner section, an actuator starts up during use of the blood treatment cassette.

In some exemplary embodiments, the actuator-sensor-mat has in the section a dent or a notch. The actuator-sensor-mat is designed such that it is not in contact with the actuator-sensor-plate in the area of its dent or notch.

In specific exemplary embodiments, the actuator-sensor-mat is in direct or indirect contact with blood treatment cassette. Thereby, the actuator-sensor-plate and/or the actuator-sensor-mat comprise in a section, which is in contact with the valve base of the valve, a rigid hump which is however not changeable by means of the blood treatment cassette in its height, adjustment or arrangement. The hump may be an enforcement of the mat materials.

In certain exemplary embodiments, the enforcement may be a buckling and may project 1 to 3 times over the main extension plane of the actuator-sensor-mat towards the blood treatment cassette.

In certain exemplary embodiments, the valve base does not comprise any undercuts.

The film valves described herein are also referred to as phantom valves, as, in a closed state with respect to the concerned channels, they do not constitute any change of the flow area compared to channel points or chambers without film valves. They are not noted or seen or perceived with regard to the flow area like a phantom.

In certain exemplary embodiments, the hump, also denoted herein as a spacing device, locally buckles the section of the film lying above it through direct or indirect contact with the latter. In this manner, it creates a space between the concerned film section and an adjacent channel bar and/or the valve base. Thereby, in some exemplary embodiments, the hump protrudes over the standard plane of the flat film, parallel thereto or falling close therewith, i.e. over the plane in which the film is essentially lying flat on the hard part, e.g. above the gluing or welding plane, also denoted herein as main extension plane of the connection. This may advantageously create a safety distance which allows a reliable flow through the valve being held open.

In some particular exemplary embodiments, the hump is arranged to locally keep the film at the standard level of the flat film even in case of under-pressure. Due to the fact that the hump does not lift the film in the area of the valve beyond the standard level, an unwanted and possibly irreversible expansion of the film section may hereby be advantageously prevented.

In certain exemplary embodiments, the hump is arranged in the hard part in a springy and/or flexible manner.

In some particular exemplary embodiments, the blood treatment cassette comprises not only one hump, rather several humps for which the same as for said hump may apply as well.

In certain exemplary embodiments, several humps (also generally denoted herein as elevations) are arranged in at least one row parallel to the course of the sealing seat bar or valve base. This arrangement may advantageously keep, with regard to fluidics, enough space between the film and the sealing seat bar or the valve base even if the humps are designed not to project above or beyond to project only slightly above or beyond the channel edge bars with which the film is connected. The flow cross-section is created or determined by the length of the passage between the valve base and the film generated by the spacer.

In certain exemplary embodiments, the hump/humps is/are furnished or covered by or provided with drainage structures. The drainage structures reduce a contact area between hump(s) and film during the sterilization and may therefore advantageously contribute to an increased effectiveness of the sterilization process.

In some exemplary embodiments, the humps are positioned at or on one or more spring elements.

In some exemplary embodiments, the hump is placed such that a space between the film section and the valve base is ensured which allows a gas or vapor exchange across the valve, i.e. between film and valve base.

In certain exemplary embodiments, the hump impacts or acts on the film from an interior of the blood treatment cassette, i.e. from a space between hard part and film.

In some exemplary embodiments, the blood treatment apparatus comprises a sub-divided or laminated pressure stamp or pressing stamp as actuator. The sub-division or lamination allows the actuator to respond to the curvatures of the valve base.

In certain exemplary embodiments, the sub-divided or laminated pressure stamp comprises a friction-free bearing arrangement for solid joints and/or a spring support.

In some particular exemplary embodiments, the blood treatment apparatus comprises in the actuator-sensor-unit other tolerance-compensation devices instead of or supplementary to the laminated pressure stamp or pressing stamp with a preferably friction-free bearing arrangement for solid joints and spring support. These include structured or on-the-inner-side humped actuator-sensor-mats, structured or humped actuator-sensor-plates, inserted foam materials and pressure pads, structured interposed elastomer elements and the like.

In some exemplary embodiments, the film valves described herein are those which also perform a function during the use of the blood treatment cassette. In other exemplary embodiments, the film valves only serve as valves with which a flow of sterilization agent between chamber and channel/chamber shall be ensured before the use of the blood treatment cassette. In these embodiments, the film valve remains closed by means of the actuator after the beginning of the blood treatment session.

Some or all embodiments may exhibit one or more of the above or below mentioned advantages.

During the sterilization of the blood treatment cassette with gases or vapor, usually several changes between vacuum and excess pressure phases take place for the gas exchange. Thereby the remaining neither welded nor glued sealing seat areas of the valves act as flow resistances. At the change or switchover from vacuum to excess pressure, they occasionally and unintentionally even act as check valves in case the film becomes deformed towards the cavities and chambers of the blood treatment cassette due to the delayed pressure compensation in the blood treatment cassette. Thereby, it is possible that the film valves close and therefore hamper or even prevent sterilization gases to enter into single channels or chambers resulting in a poor or insufficient sterilization. So far, one had to revert to uneconomical sterilization methods to solve this problem. These disadvantages may be reduced or avoided by means of the blood cassette due to the fact that, thanks to the spacer, its film valves remain open even when negative pressure is applied during the sterilization process.

Due to the provided hump, which maintains the film, disposed above the film valves, on which the said film is not welded on the hard part, under stress, mechanical stresses of the non-welded film section or portion resulting from the change or transition from vacuum to excess pressure and vice versa may be prevented or at least reduced. This may counteract a sagging of the films resulting from mechanical stress as well.

A technical solution is thus proposed which advantageously allows the film at one point or at several points of the boundaries of the chambers and channels to be spaced apart from the hard part such that a fluidic connection builds up between the chambers and the channels analogous to the functionality of the phantom valve described already. Therewith, the transport of the sterilization gas is improved and the film stress generated due to pressure changes is reduced.

A further advantage is that in connection with an already slightly dented film due to a manufacturing tolerances, it may nevertheless be excluded that the film, in the area of the valve sealing seat edges, may start a contact over a large area thereof prior to the gas sterilization treatment. It remains rather locally spaced until the blood treatment cassette has completed the sterilization process.

By using the actuator-sensor-unit, the tolerance-balance or tolerance-compensation devices may hereby advantageously maintain the sealing effect of flat or dented film valves and are robust against dimensional tolerances of the blood treatment cassette, the blood treatment device or the alignment between blood treatment cassette and blood treatment apparatus.

BRIEF DESCRIPTION OF THE FIGURES

The present invention shall be exemplarily explained in the following by way of the accompanying drawings, in which identical reference numerals designate same or similar elements. In the partially simplified figures.

The standard arrows in the figures indicate the direction of the blood stream. The block arrows indicate the respective direction of the substituate stream.

DETAILED DESCRIPTION

Figure 1:
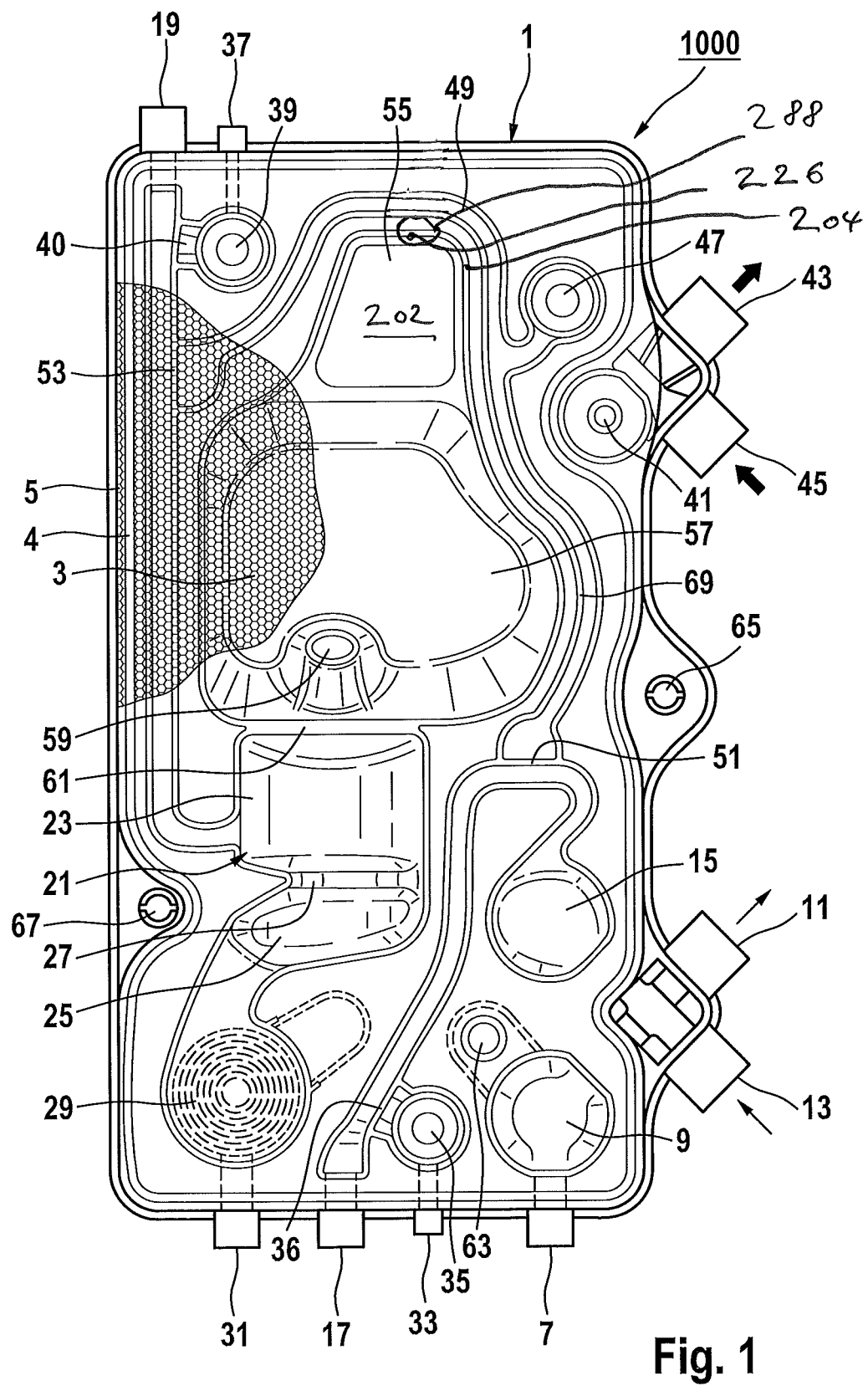
FIG. 1 shows a lateral view of a blood treatment cassette provided in accordance with an embodiment, having a cover on its front side.

FIG. 1 shows a lateral view of a blood treatment cassette 1000 which is provided with a cover device at the surface one looks upon in FIG. 1.

In the following, the blood treatment cassette 1000 is also referred to as cassette 1000 in short.

The cassette 1000 comprises a hard part 1. As it is exemplarily shown in FIG. 1, the hard part 1 comprises chambers, channels and valves. As it is furthermore exemplarily shown in FIG. 1, the chambers, channels and valves are integrated into the hard part 1 or are at least partly formed by the hard part 1.

The cassette 1000 of FIG. 1 is provided at its front side with a cover, here, for example, a film 3. The cover may be welded in a flat manner, i.e., planarly, onto the hard part 1.

An embodiment involving a three-dimensional configuration of the welding and sealing contour is also possible.

The cover device may close the chambers or channels of the hard part 1 of the cassette 1000, namely, against a side of the cover means facing away from the hard part 1 or against the atmosphere.

As seen in FIG. 1, the film 3 rests on the hard part 1 of the cassette 1000 at a closed sealing bar 4. The film 3 is welded on the hard part 1 of the cassette 1000 at a closed weld 5.

The closed sealing bar 4 may alternatively be realized in an exposed manner.

The film 3 may be connected to the hard part 1 of the cassette 1000 at additional local welds (not shown). These may also be closed or peripheral, i.e. closed in the sense of an enclosing limitation similar to a ring, or dot-shaped.

The film 3 may locally be connected, e.g. welded, to the hard part 1 of the cassette 1000 in form of dots or a line, in particular at the edge zones of the liquid-conducting channels.

The film 3 may be connected to the hard part 1 of the cassette 1000 by laser welding. If so, it is advantageous if heat is locally applied while using a light-absorbing component. The light-absorbing component may be part of the material of the film or of the hard part, or a layer disposed between film and hard part or above the film. The layer may be a film layer.

The cassette 1000 may at least be coupled with a blood treatment apparatus (not shown in FIG. 1) at its front side shown in FIG. 1. An exemplary technique for suitable coupling of a cassette 1000 to a coupling surface of a blood treatment apparatus is described in the patent applications 10 2009 012 633.3 having the title "Vorrichtung zum Verbinden einer externen Funktionseinrichtung mit einer Anordnung, Anordnung aufweisend eine solche Vorrichtung und Verfahren zum Verbinden" [Device for connecting an external functional means to an arrangement, arrangement including a like apparatus, and connecting method] as filed with the German Patent and Trademark Office on Mar. 10, 2009, and 10 2009 012 632.5 having the title "Abdichtungseinrichtung zum Abdichten eines Volumens einer medizinischen Behandlungsanordnung gegen ein weiteres Volumen sowie Anordnung und Verfahren" [Sealing means for sealing a volume of a medical treatment arrangement against another volume, as well as arrangement and method] also filed with the German Patent and Trademark Office on Mar. 10, 2009, the respective disclosures of which are herewith fully incorporated by way of reference.

The cassette 1000 may be coupled with a coupling surface of the blood treatment apparatus by the plane of the film 3 or through the intermediary of the latter. The coupling area may preferably be executed three-dimensionally.

The coupling surface of the blood treatment apparatus may be inclined to the rear, for instance at an upper portion thereof shown in FIG. 1, by 8 degrees against a vertical line extending from top to bottom in FIG. 1 (in the direction extending from the observer into the plane of drawing in FIG. 1).

The cassette 1000 comprises an arterial patient connection 7.

The cassette 1000 comprises an arterial pressure measurement chamber 9. The latter may include corresponding sensors. The sensors may transmit signals, preferably through the intermediary of cables or cabling. The sensors may, however, also be provided to transmit signals in a wireless manner.

The cassette 1000 comprises a connector 11 for the exit of blood from the cassette 1000 as well as a connector 13 for the entry of blood into the cassette 1000.

The two connectors 11 and 13 are adapted to be connected to a pump tube segment or pump tube set of a blood pump.

The cassette 1000 further comprises a chamber 15 including a pressure measurement site for pressure measurement in the extracorporeal blood circuit upstream from the dialyzer ("pre-filter") or downstream from the pump ("post-pump"), respectively.

At the chamber 15 the pressure in the extracorporeal circuit upstream from the dialyzer may be measured across the film 3 or via the film 3.

The cassette 1000 comprises an arterial filter conduit 17 as well as a venous filter conduit 19.

The interior of the cassette 1000 comprises a venous blood chamber 21. The venous blood chamber 21 is subdivided into an upper space 23 and a lower space 25.

The upper space 23 of the venous blood chamber 21 may admit a laterally tangential inflow of blood. Here, blood may flow in laterally through the inlet (on the left side in FIG. 1) into the upper space 23 and spread out tangentially to the walls of the upper space 23. A laterally tangential inflow of blood may create a zone with a substantially or completely stable rotational flow of blood in the upper space 23 of the venous blood chamber 21.

The lower space 25 of the venous blood chamber 21 may represent a calming zone for the blood stream. Such a calming zone may possibly have substantially no rotational flow or no rotational flow of the blood present therein at all.

The venous blood chamber 21 is subdivided into the upper space 23 and the lower space 25 by a cross-sectional restriction 27 of the hard part 1 of the cassette 1000. The cross-sectional restriction 27 reduces the cross-section of the venous blood chamber 21 in its width and depth so as to result in a shoot or rapid, whereby a fluid having traversed the cross-sectional restriction 27 will flow with slower flow velocity through the venous blood chamber 21 of the cassette 1000. The upper space 23 and the lower space 25 are in fluid communication.

By using such a construction, i.e., a subdivision of the venous blood chamber 21 into a zone with substantially or completely stable rotational flow of the blood and a calming zone for the blood stream, it is advantageously possible to achieve an efficient separation of air from the blood or fluid.

Walls of the upper space 23 and of the lower space 25 of the venous blood chamber 21 may suitably be adapted to an inclination from the vertical position of the upper portion of the cassette 1000 in FIG. 1, for example, an inclination to the rear by 8 degrees (into the plane of the drawing) of the upper part of the cassette 1000 shown in FIG. 1. They may suitably have a rounded shape such that they advantageously represent a flow-optimized contact surface for fluids passing through the venous blood chamber 21.

The cassette 1000 comprises a clot trap 29.

The clot trap is preferably a clot trap as disclosed in the patent application (10 2009 024 495.6) having the title "Gerinnselfänger, externe Funktionseinrichtung, Blutkreislauf sowie Behandlungsvorrichtung" [Clot trap, external functional means, blood circuit and treatment apparatus] to the applicant of the present invention that was filed with the German Patent and Trademark Office on Jun. 10, 2009. The relevant disclosure thereof is herewith fully incorporated by way of reference.

At the clot trap 29, it is possible to measure the pressure in the extracorporeal circuit through the film 3 or across the film 3, i.e., in particular after passage through the dialyzer or downstream of the dialyzer.

The cassette 1000 comprises a venous patient connection 31.

The cassette 1000 comprises an arterial heparin addition site 33. Here, it should be noted that the heparin addition site 33 (just like a venous heparin addition site 37) may also be suited and intended for adding other pharmacologically effective agents than heparin, which are only in a preferred manner anti-coagulants or combinations of active agents. This should also be noted whenever heparin is mentioned previously or in the following in any kind of context.

The cassette 1000 comprises a check valve 35 at the arterial heparin addition site 33.

Exemplary check valves for the use as check valve 35 of the arterial heparin addition site 33 and also as further check valves of the cassette 1000 are disclosed in the patent application to the applicant of the present invention 10 2009 024 469.7 having the title "Ventilvorrichtung, Ventileinsatz, externe Funktionseinrichtung, Behandlungsvorrichtung sowie Verfahren" [Valve device, valve insert, external functional means, treatment apparatus, and method] as filed with the German Patent and Trademark Office on Jun. 10, 2009, the relevant disclosure of which is herewith fully incorporated by way of reference.

The cassette 1000 comprises an arterial heparin addition valve 36. By using the arterial heparin addition valve 36 the addition of heparin into the arterial filter conduit 17 may be controlled or regulated.

The arterial heparin addition valve 36 may be configured as a so-called phantom valve.

The expression "phantom valve" as used herein designates an element having an actor surface (in the present case, for example, an actor membrane) that may be reached by an actor that may adopt the function of a valve.

The actor membrane can be made to move, dilate, curve, etc. in one direction by applying a force on it, e.g., a pressing force. As a result of its movement or dilatation, the actor membrane may come into contact with an element such as a sealing device, e.g. a bar, or move away from the latter. The actor membrane may thus, for example, effect or enhance or terminate or reduce a sealing effect.

When the force acting on the actor membrane is ceased to apply or is released, the latter may return, for example, to a basic position, e.g., a non-bent condition.

A phantom valve for use as an arterial heparin addition valve 36 as well as further phantom valves of the cassette 1000 may be configured with or from a bar portion of a channel at the hard part 1 of the cassette 1000 and a portion of the film 3 contacting or facing the bar portion.

Phantom valves may be operated through actors of the blood treatment apparatus.

In order to close a phantom valve, the portion of the film 3 may be pressed onto the bar portion. In order to open the phantom valve, the portion of the film 3 may again be raised or removed from the bar portion.

Further examples of phantom valves may be found in the patent application 10 2009 012 632.5 having the title "Abdichtungseinrichtung zum Abdichten eines Volumens einer medizinischen Behandlungsanordnung gegen ein weiteres Volumen sowie Anordnung und Verfahren" [Sealing device for sealing a volume of a medical treatment arrangement against another volume, as well as arrangement and method], as filed with the German Patent and Trademark Office on Mar. 10, 2009 by the present applicant besides the patent application DE 100 53 441 A1 and the patent application (DE 102 24 750 A1). The relevant disclosures thereof are herewith fully incorporated by way of reference.

The cassette 1000 comprises a venous heparin addition site 37. The venous heparin addition site 37 may be configured as a Luer-connector.

The cassette 1000 comprises a check valve 39 at the venous heparin addition site 37.

The cassette 1000 comprises a venous heparin addition valve 40. With the aid of the venous heparin addition valve 40 the addition of heparin into the venous filter conduit 19 may be controlled or regulated.

The cassette 1000 comprises a substituate addition site 41 or a substituate connector, respectively.

The substituate addition site 41 may be a connection means as it is described in the patent application 10 2009 024 575.8 to the present applicant having the title "Verbindungseinrichtung und Verfahren zum Verbinden wenigstens zweier fluidführender medizintechnischer Systeme, sowie medizintechnische Vorrichtung" [Connection means and method for connecting at least two fluid-conducting medical-technical systems, as well as a medical-technical apparatus] as filed with the German Patent and Trademark Office on Jun. 10, 2009 by the present applicant. The relevant disclosure thereof is herewith fully incorporated by way of reference.

The substituate addition site 41 may be provided with a touch-protection element (not shown). The substituate addition site 41 may be provided with a drip-protection element (not shown). The drip-protection element may be realized through an integrated closure sleeve. The drip-protection element may prevent residues of substituate or blood from dripping out when the cassette 1000 is released and subsequently removed from the blood treatment apparatus.

The drip-protection element may be designed to be removable. It may be configured as a hood or lid.

The substituate addition site 41 or some other portion of the cassette 1000 may moreover provide a tamper protection, as a result of which the user recognizes effortlessly, or at one glance, whether the cassette 1000 has already been used. This tamper protection may be realized by means of the touch-protection element, the closure sleeve, or some other structure. Preferably, the corresponding structure may recognizably change its position inside or relative to the cassette 1000. Preferably it may change its shape.

Moreover, the substituate addition site 41 or some other portion of the cassette 1000 may provide a protection against reuse. In a preferred manner, the cassette 1000 is made unusable by means of a closure sleeve—preferably in an irreversible manner—with respect to an attempted reuse. If the cassette 1000 should nevertheless be used again, sensors of the blood treatment apparatus do not measure the signal characteristics that would be measured during use of a new cassette. This may be due to the fact that liquid cannot enter into the cassette 1000 or into the substituate addition site 41, or at least not in a sufficient or usual quantity. The control unit of the blood treatment apparatus may recognize this. A warning may be triggered.

As a tamper protection or a protection against reuse it is preferably possible to use a tamper protection or protection against reuse as disclosed by the applicant of the present invention in the patent application 10 2009 024 575.8 having the title "Verbindungseinrichtung und Verfahren zum Verbinden wenigstens zweier fluidführender medizintechnischer Systeme, sowie medizintechnische Vorrichtung" [Connection means and method for connecting at least two fluid-conducting medical-technical systems, as well as a medical-technical apparatus] that was filed with the German Patent and Trademark Office on Jun. 10, 2009. The relevant disclosure thereof is herewith fully incorporated by way of reference.

The cassette comprises a connector 43 for the exit of substitute from the cassette 1000 as well as a connector 45 for the entry of substitute into the cassette 1000.

The connectors 43 and 45 are adapted to be connected to a pump tube segment or a pump tube set of a substitute pump.

The cassette 1000 comprises a check valve 47 for the addition of substitute.

Substitute may be introduced into a substitute conduit 49 by operating the check valve 47.

The cassette 1000 comprises a pre-dilution addition valve 51. The pre-dilution addition valve 51 may be configured as a phantom valve.

The cassette 1000 comprises a post-dilution addition valve 53. The post-dilution addition valve 53 may be configured as a phantom valve.

The cassette 1000 comprises a single-needle sterile membrane 55.

The cassette 1000 comprises a single-needle chamber 57. In FIG. 1, the single-needle chamber 57 is disposed above the venous blood chamber 21.

Inside the single-needle chamber 57 a blood surge redirection element 59 is arranged. The blood surge redirection element 59 may serve for decelerating a blood surge or distinguishing its impulse.

A connection to an inside of the single-needle chamber 57 may be provided by means of connection means as disclosed by the applicant of the present invention in the patent application 10 2009 024 467.0 having the title "1Einrichtung sowie externe Funktionseinrichtung und Behandlungsvorrichtung zum Behandeln von medizinischen Fluiden" [Device and external functional means and treatment apparatus for the treatment of medical fluids] that was filed with the German Patent and Trademark Office on Jun. 10, 2009. The relevant disclosure thereof is herewith fully incorporated by way of reference.

The cassette 1000 comprises a single-needle blood valve 61. The single-needle blood valve 61 may be configured as a phantom valve.

The cassette 1000 comprises an evacuation site 63. The evacuation site 63 may serve for vacuum coupling of the cassette 1000 to the blood treatment apparatus as is described, for example, in the patent application DE 10 2007 042 964 A1 having the title "Vorrichtung und Verfahren zur Behandlung einer medizinischen Flüssigkeit" [Apparatus and method for treating a medical liquid] that was filed with the German Patent and Trademark Office on Sep. 10, 2007. The relevant disclosure thereof is herewith fully incorporated by way of reference.

The cassette 1000 comprises a primary alignment center 65. The primary alignment center 65 may advantageously serve for aligning or latching of the cassette 1000 on the blood treatment apparatus.

The cassette 1000 comprises a secondary alignment site 67. The secondary alignment site 67 may serve for aligning or latching of the cassette 1000 on the blood treatment apparatus.

The cassette 1000 is filled with gas (e.g., sterile air) prior to beginning priming. During priming of the extracorporeal blood circuit this gas filling has to be displaced. Insofar, a blood treatment cassette generally represents a particular challenge as there are both rising and falling conduits and moreover chambers in which no "air nests" must remain. For this purpose, the present cassette 1000 is provided with special construction features:

The chamber 15 for measuring the arterial pressure is constructed such that air may rise into a pump tube segment (e.g. into the pump tube segment). Advantageously, there are no dead spaces present. Air rising by itself from the arterial pressure measurement chamber into the pump tube segment of the blood pump is forcibly conveyed through the pump tube segment from the engagement range of the blood pump (e.g., by the rollers of a roller pump). As soon as the pump ceases to exert an influence (for example due to disengaging the rollers), the air rises by itself into the cassette 1000 in the conveying direction.

The venous recirculation conduit (or a venous portion of the extracorporeal circuit) is a downward conduit. Starting from a particular prevailing volume flow (e.g., 200 ml/min in the case of the cassette 1000 shown in FIG. 1), air bubbles in the blood are "entrained" even against gravitational acceleration or gravitation. This effect is made use of in the downward conduits. The conduit cross-sections of the downward conduits are designed with such a small size that a forcible conveyance of the air bubbles even against gravitational acceleration is successful due to the flow velocity.

In the venous blood chamber 21 large cross-sections are provided, such that air bubbles may reliably rise there against the main direction of flow due to the slower or lower flow velocities present in this location.

Further constructive features of the cassette 1000 are as follows:

The phantom valves 40, 51 and 53 are arranged such that blood (which has a higher density than water or substitute etc.) can hardly penetrate "upward" or "sideways" into opened phantom valves while the cassette 1000 is operated with blood, for the latter descends as compared to the lighter water. Such an advantageous arrangement is achieved with the aid of the phantom valves 40, 51, and 53. The valve 36, on the other hand, does not imply such a requirement, i.e., the arrangement is not crucial there.

For the same reason, the conduit channel (stub channel) below the check valve 47 for adding substitute is constructed or arranged in a rising manner. In the event of a malfunction of the pre- or post-dilution valves 51 and 53 and a resulting bypass flow of blood, blood cannot rise into the substitute conduit 49 anymore. The blood will rather flow past the opening of the corresponding stub conduit.

The inclination of the cassette 1000 preferably is from 5 degrees to 11 degrees, in a particularly preferred manner it assumes the 8 degrees already mentioned above.

Reference numeral 288 denotes a phantom valve which allows in the first position a flow in the chamber 202 or prevents it in a second position. In its simplest embodiment, a phantom valve is a film valve through which a fluid path, between hard part 1 and the section of the film disposed above it, is prevented through temporary pressing of the film 3 on a valve base, like a bar or other sections of the hard part 1, and reopened after release of the pressing force.

The reference numeral 202, 204 and 226 are elucidated in the description of FIGS. 4 to 9.

Figure 2:
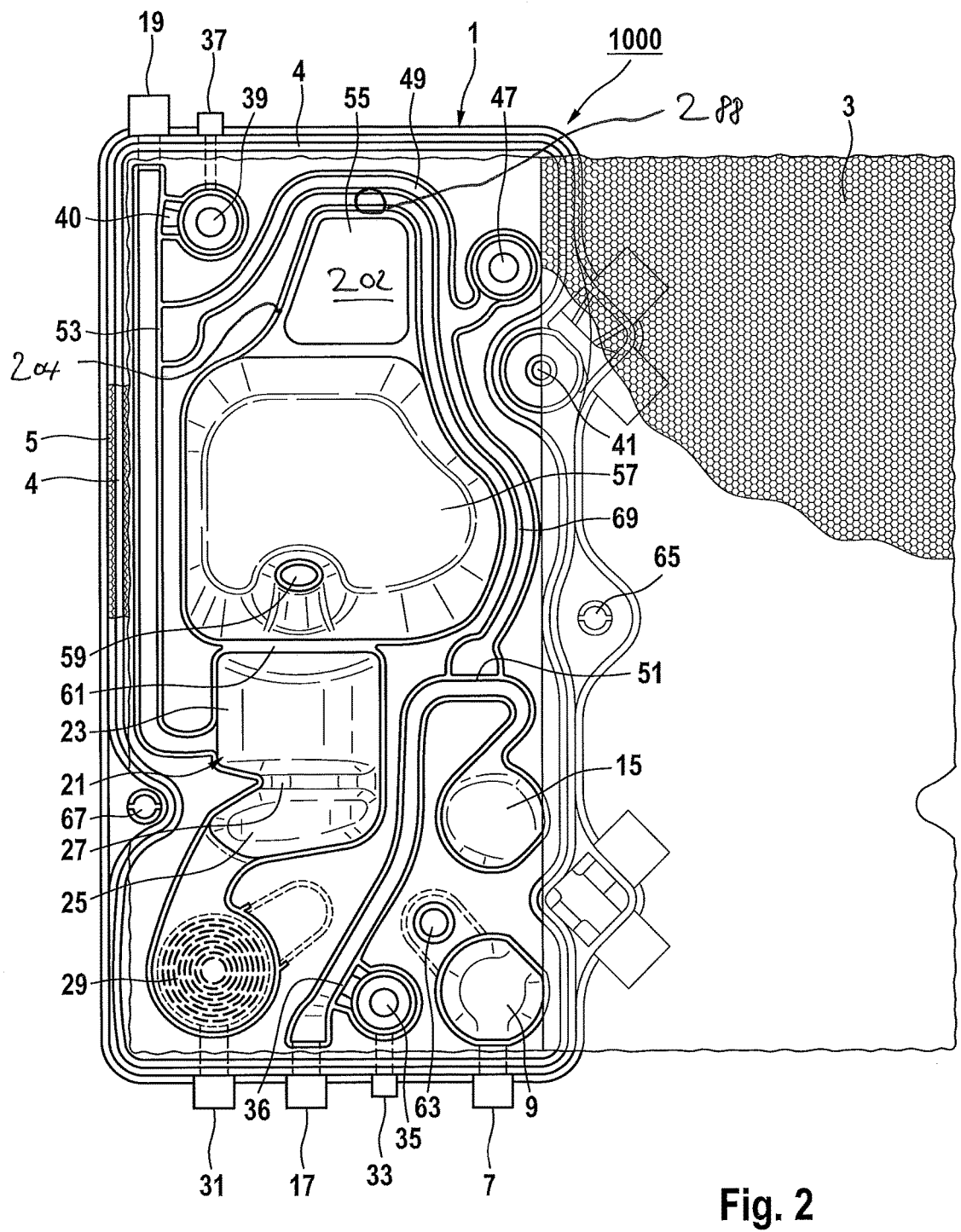
FIG. 2 shows the external functional device of FIG. 1 with the cover means swung-open following destructive cutting.

FIG. 2 shows the cassette 1000 of FIG. 1, wherein the film 3 is recognized to be cut open destructively at the left-hand margin of the cassette 1000 as well as at the top and bottom and swung open to the right for better illustration.

As is shown in FIG. 2, the film 3 comprises a surface texture.

FIG. 2 shows the elements inside the cassette 1000 which are visible in more detail after having cut open the film 3.

In order to avoid repetitions, reference is made to the configurations of the aforesaid individual elements discussed in the description of FIG. 1.

Here, it is clearly seen that the cassette 1000 comprises a sealing bar 69. The sealing bar 69 may be employed, for example, for realizing the pre-dilution addition valve 51.

Figure 3:
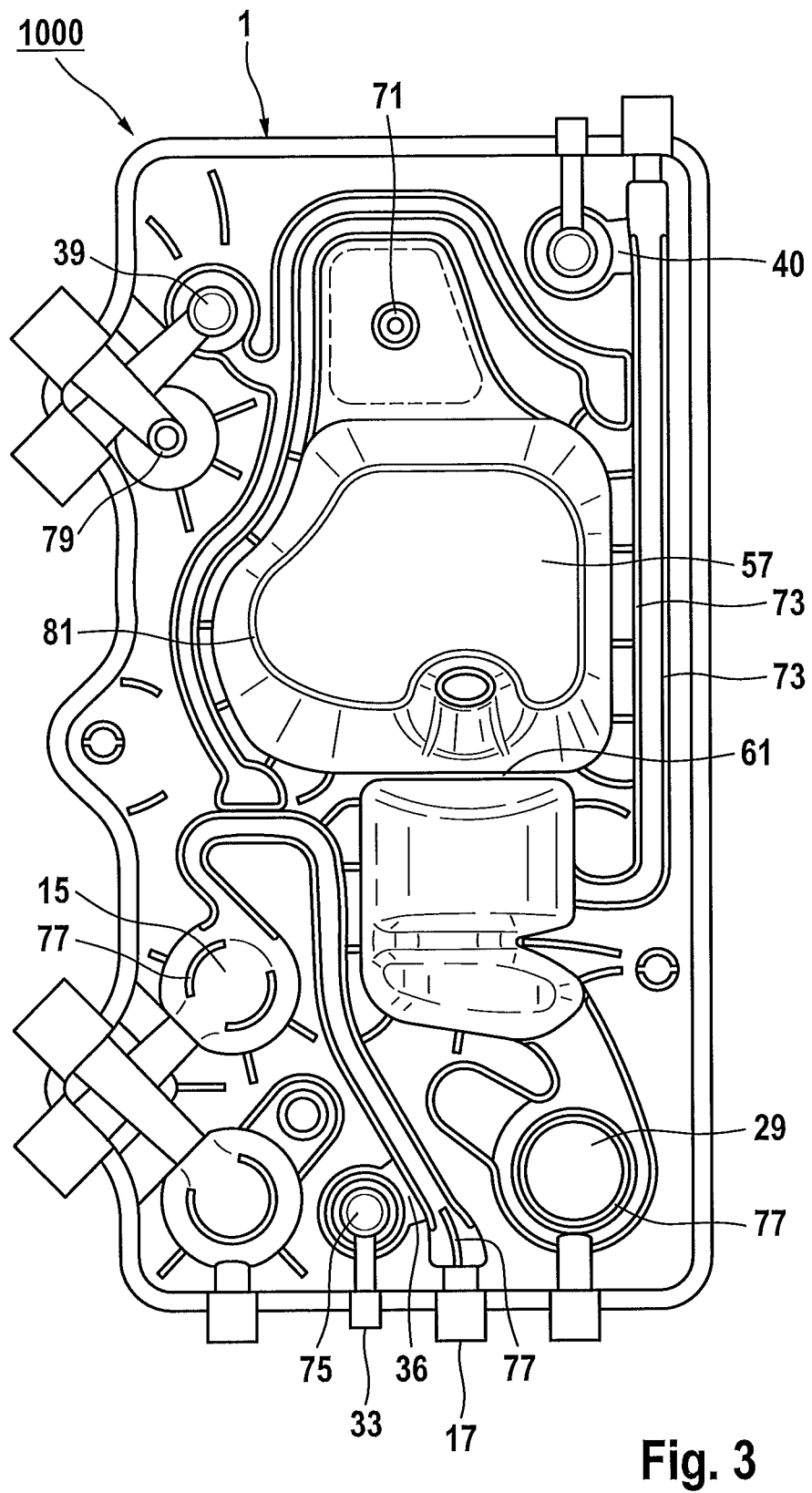
FIG. 3 shows the blood treatment cassette of FIG. 1 and FIG. 2 from its rear side.

FIG. 3 shows the cassette 1000 from its rear side. When the cassette 1000 is coupled with the blood treatment apparatus, an observer opening a door of the blood treatment apparatus for removing the cassette 1000 will look upon this rear side.

The cassette 1000 comprises a single-needle air connector 71. It may be provided to arrange a support grid (not shown) of the single-needle sterile membrane 55 at the single-needle air connector 71 on the apparatus side or on the blood side.

The cassette 1000 comprises several support bars. The support bars have different heights relative, e.g., to the plane of the film 3. The support bars are projected in the side of the cassette 1000 facing the observer in FIG. 3, i.e., out of the plane of drawing of FIG. 3.

The cassette 1000 comprises support bars 73 having a height of 5 mm, support bars 75 having a height of 8 mm, support bars 77 having a height of 13 mm, support bars 79 having a height of 24 mm, and support bars 81 having a height of 31 mm. These and other numeric values should, of course, be understood as mere examples.

The support bars may serve to support the cassette, in the state of being coupled to a blood treatment apparatus, against a lid of a reception portion of the blood treatment apparatus for receiving the cassette. Exemplary embodiments of such a coupling of the cassette to the blood treatment apparatus are given in the patent application 10 2009 012 633.3 having the title "Vorrichtung zum Verbinden einer externen Funktionseinrichtung mit einer Anordnung, Anordnung aufweisend eine solche Vorrichtung und Verfahren zum Verbinden" [Device for connecting an external functional means to an arrangement, arrangement including a like apparatus, and connecting method] as filed with the German Patent and Trademark Office on Mar. 10, 2009, the relevant disclosure of which is herewith fully incorporated by way of reference.

In FIG. 3 the cassette 1000 is shown as it will be viewed by the user/observer after its coupling to the machine interface. The inclination of the cassette 1000 relative to the machine is realized with a "rearward inclination", so that the upper edge is located at a further distance from the user/observer than the lower edge.

The upwardly-facing surfaces of the venous blood chamber 21 and of the single-needle chamber 57 accordingly comprise such an inclination that air bubbles may still reliably rise on the inside despite the inclination of the cassette 1000. As an alternative, a cassette design which does not provide any inclination of the cassette is, of course, basically also possible.

The following figures show sections of a cassette 1000 which may by all features be in accordance with the cassette 1000 of FIGS. 1 to 3, as long as it does not deviate in the following described embodiments therefrom. In any case, the cassette 1000 of the following figures may comprise features of the cassette 1000 shown in FIG. 1 to FIG. 3 as long as the respective features combinations is not realized by the skilled person to be technically impossible.

Figure 4:
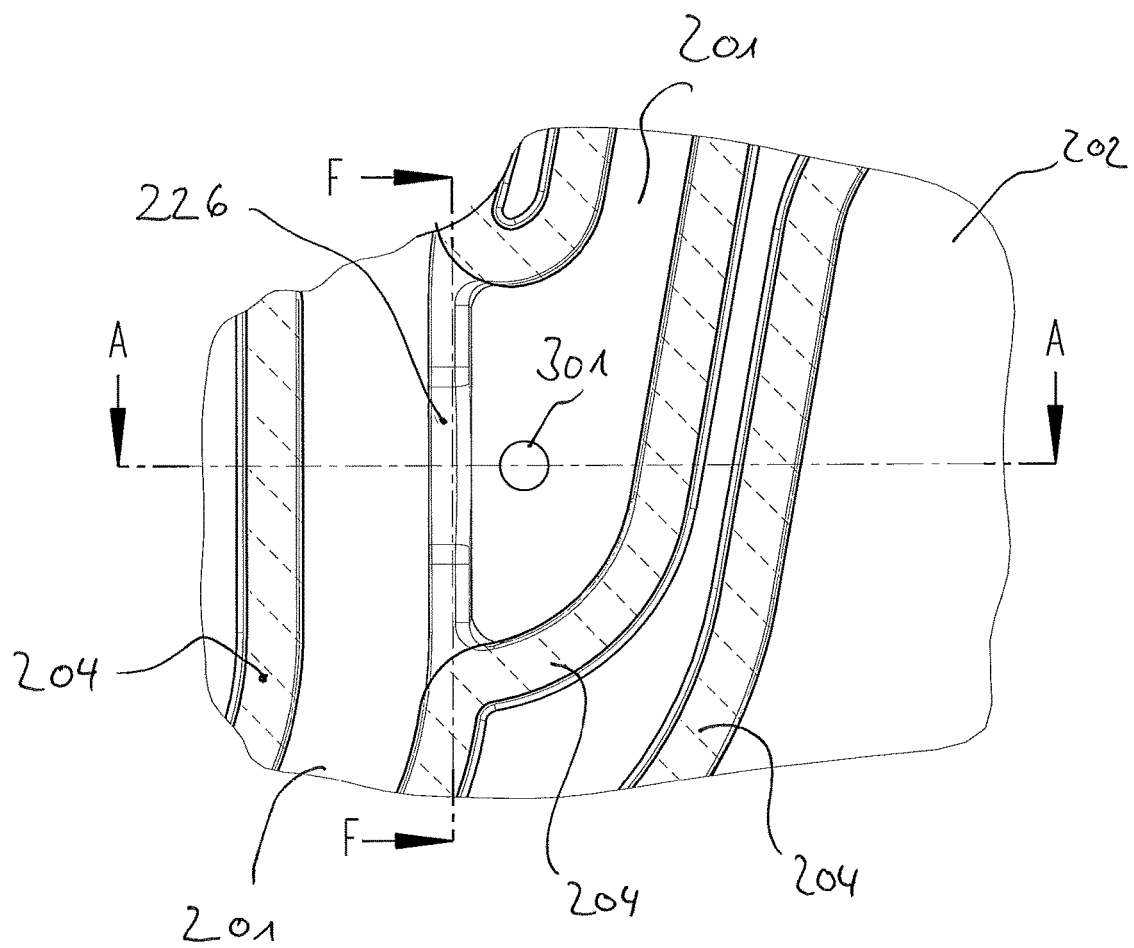
FIG. 4 shows in a top view a section of a hard part of a blood treatment cassette.

FIG. 4 shows, in a top view, a section of a hard part 1 of a cassette 1000, for example the one of the aforementioned figures. The hard part has channels 201, a chamber 202, closed, flat channel edge bars 204 at which the film 3 is glued to or welded on the hard part 1. Furthermore, a section 226 of the hard part 1, realized as dented, is illustrated which continues into the channel edge bar 204 or interrupts it. The film 3 is not glued to or welded on the section 226 of the hard part 1 disposed beneath it, thus enabling the valve effect mentioned supra. The section 226 is herein denoted as a film sealing seat-bar 226. Instead of the dented configuration as shown in FIG. 4, the section 226 may also be flat or straight.

The reference numeral 301 denotes a hump, which is arranged in the vicinity of the valve base 226 and, purely optional, in the channel 201. The cassette-sided hump 301 may be provided elsewhere in the cassette 1000, for example in the chamber 204. However, it must be arranged at a suitable distance from the to-be-held-open valve.

Figure 5:
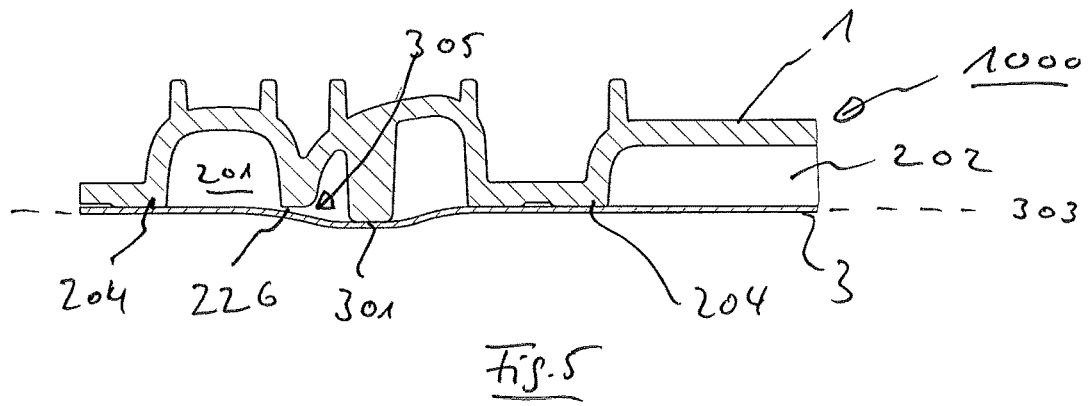
FIG. 5 shows the view of the blood treatment cassette illustrated in FIG. 4 in a first embodiment towards the arrow A of FIG. 4.

FIG. 5 shows a view of the cassette 1000 illustrated in FIG. 4 in a first embodiment towards the arrows A of FIG. 4.

FIG. 5 shows the arrangement of the hump 301 in a first embodiment in which it extends beyond a main extension plane 303 of the connection between the film 3 and hard part 1 or projects beyond it. The main extension plane 303 (shown in dashed line in FIG. 5) may in some particular embodiments with a completely flat film 3, such as exemplarily shown in FIG. 6, be, for the sake of simplicity, equated with the plane in which the film extends substantially.

The hump 301 recognizably maintains a distance of the film 3 to the valve base 226, resulting in the gap 305. The latter is used to optimize the sterilization by gas or steam as discussed above. The valve base 226, as it is shown in FIG. 5, may be present in the main extension plane 303 just as the channel edge bars 204 may also be.

Figure 6:
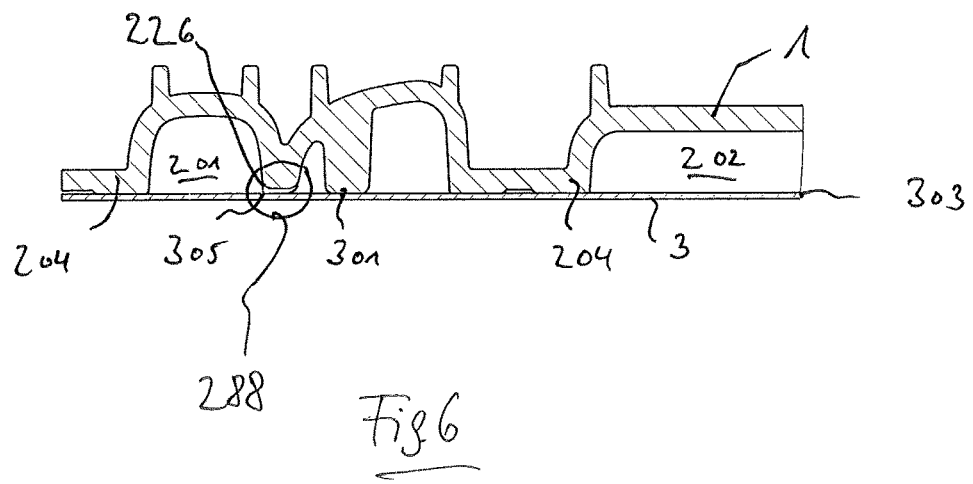
FIG. 6 shows the view of the blood treatment cassette illustrated in FIG. 4 in a second embodiment again towards the arrow A of FIG. 4.

FIG. 6 shows a view of the cassette 1000 illustrated in FIG. 4 in a second, possible embodiment, again towards the arrows A of FIG. 4.

FIG. 6 shows the arrangement of the hump 301 in which it does not extend beyond a main extension plane 303 of the connection between the film 3 and hard part 1 or project beyond it.

Figure 7:
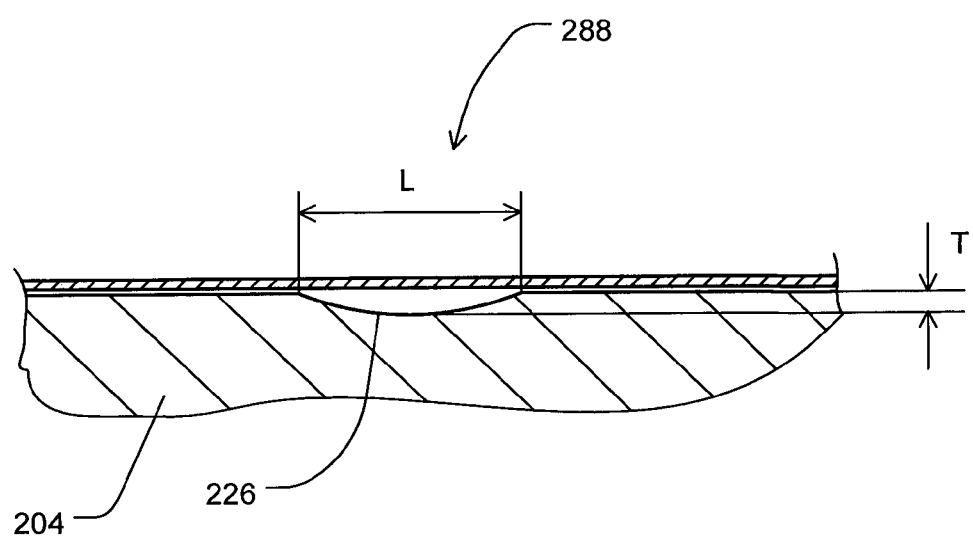
FIG. 7 shows a valve of the blood treatment cassette.

In the illustrated exemplary case of FIG. 6, the section 226 is optionally dented or not straight, and has a dent depth T, dent width L and valve base or sealing seat bar length L; for a better understanding of the aforesaid measurements see FIG. 7, wherein the non-illustratable dent width B extends into the drawing plane.

The embodiment of FIG. 6 differs from that of FIG. 5 in that the hump 301 does not protrude out of or extends beyond the main extension plane, rather its hump peak touches the film 3. In addition, the valve base 226 is not in the main extension plane 303.

The hump 301, nevertheless, maintains a distance of the film 3 to the valve base 226, as it ensures that the gap 305 is maintained also in the case of vacuum and the film 3 cannot lean against the valve base 226.

Also in the example of FIG. 6, the hump 301 keeps the film 3 within a suitable distance apart from the base of the dent, the valve base 226.

In the exemplary embodiment described herein, the optimal width of the dent is circa 10 to 30 times the film thickness and its depth assumes circa 1 to 3 times the film thickness.

Figure 8:
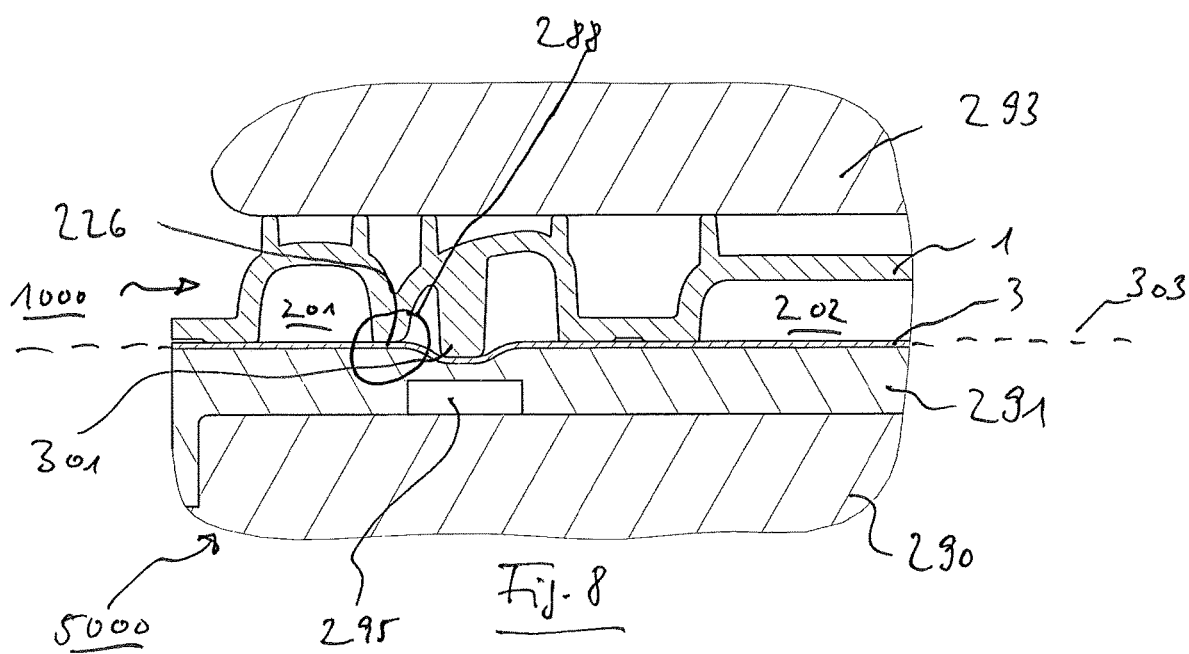
FIG. 8 shows the blood treatment cassette of FIG. 5 inserted in an embodiment of the blood treatment apparatus and pressed by it between door and actuator-sensor-mat.

FIG. 8 shows the cassette 1000 of FIG. 5, inserted in an embodiment of the blood treatment apparatus 5000 and pressed by the latter between door 293 and actuator-sensor-mat 291. The cassette is therewith shown in an equipped, ready-for-use state, namely, in sections from the side having a horizontally arranged film plane or main extension plane 303.

The actuator-sensor-mat 291 comprises a dell or notch 295 in the area of the hump 301. In the herein illustrated example, this relates only to the side of the actuator-sensor-mat 291 facing away from the blood cassette 1000. It acts as an elasticity zone and is designed such that a closing of the valve 288 by which the film 3 touches also the valve base 226 is made possible by pressing the actuator-sensor-mat 291 against the film 3. An actuator for closing the valve 288 after completion of sterilization or prior to beginning of the blood treatment is advantageously not required in this embodiment.

The notch 295 may be exemplary designed as a pocket or slot in the actuator-sensor-mat 291 or in the actuator-sensor-plate 290. Thereby, the hard bracing or support of the cassette 1000 may locally be neutralized by the actuator-sensor-plate 290.

Vacuities and flexible zones may also be created by inserting specified flexible elements such as springs, closed-cell foams, rubber ribs, etc. into the notch or pocket. The advantage of this design is that the dent in the actuator-sensor-mat 291 which is shown in FIG. 8 clears away again after the removal of the cassette 1000; this means that the actuator-sensor-mat 291 may return to be in a flat form again. In this way, the actuator-sensor-mat 291 may be cleaned in an easier and more reliable manner. In addition, such an actuator-sensor-mat 291 allows or enables an improved vacuum coupling of the film 3 of cassettes 1000 used in subsequent treatments.

Alternatively, there may be an already preformed dent in the actuator-sensor-mat 291 corresponding in its depth and form to a sufficiently high local dent of the film 3, however being below the damage limit. This dent may additionally be broadened in both directions of the film plane at the possible tolerance of the arrangement of the humps 301 to the dent of the actuator-sensor-mat 291.

Figure 9:
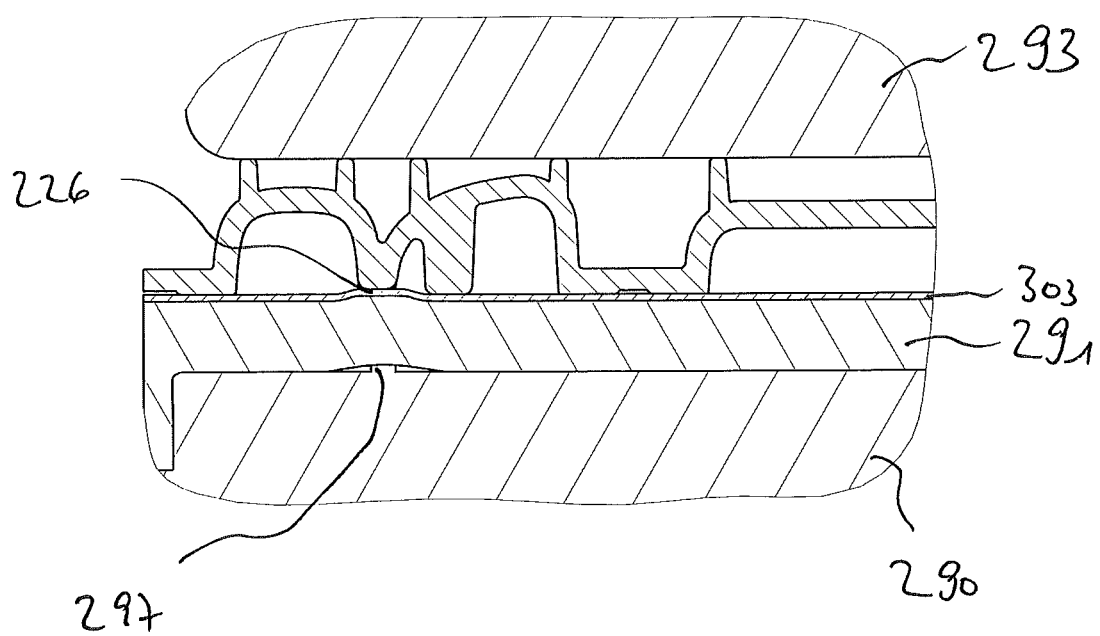
FIG. 9 shows the blood treatment cassette of FIG. 6 inserted in an embodiment of the blood treatment apparatus and pressed by it between door and actuator-sensor-mat.

FIG. 9 shows the cassette 1000 of the FIG. 6 inserted in and pressed by an embodiment of blood treatment apparatus 5000 between door 293 and actuator-sensor-mat 291. The cassette is therewith shown in an equipped, ready-to-use state, namely, in sections from the side having a horizontally arranged film plane or main extension plane 303.

The actuator-sensor-plate 290 comprises in the area of the valve base 226 an elevation or hump 297. The hump 297 might be an integral section of the actuator-sensor-mat 291; in the herein illustrated example, the hump 297 is however an added or integral component of the actuator-sensor-plate 290.

The hump 297 is provided in an area of the actuator-sensor-plate 290 assigned for the valve base 226 of the pressed cassette 1000. The hump 297 effects or acts such that it enables a closing of the valve 288 by which the film 3 touches the valve base 226 by pressing the actuator-sensor-mat, curved or dented by the hump 297, onto the film 3. An actuator for closing the valve 288 is advantageously not needed in this embodiment either.

It should be noted that the valve base or the valve-sealing seat-bar of the section 226 does not necessarily have to be dented. A straight course of the valve base is also encompassed by the present invention.

The gas-passing effect which is described with regard to the aforementioned figures may also be achieved if one higher hump or several side-by-side humps are provided which are arranged parallel to the valve-sealing seat edge, having correspondingly lower protruding height differences. In the latter case, the film valve may be designed to be longer (with regard to its spatial extension) in its extension along the channel edge according to the number of humps.

The hump 297 may be designed such that it represents or reproduces in spatial direction Y (=vertical in FIG. 4) the form of the film valve dent in the hard part 1 having the film 3 nestled above it, and maintains this form in spatial direction X (=horizontal in FIG. 4) across the width of the valve bar or valve base 226 plus the double-sided positioning tolerance so that it again adapts in the plane of the actuator-sensor-plate 290 in a rounded manner. In order for the valve 288 to transform from a flat, initial form by closing and pressing of door 293 into an adapted, deformed or buckled form which is pressed tightly at the dented valve sealing edge, not only a sufficient flexibility is required, rather also a local pressing force. The general pressing force of the machine door 293 on the entire cassette 1000, after having been equipped, may, in some versions of the cassette with gluings or weldings that are flush along the channel edge, be selected to be too small in order to ensure a sufficient sealing pressure of the film valve sealing bars against the film 3. For this reason, an increased pressing is advantageously provided locally. This may be effected in that the buckling, which is raised by the hump 297, is designed to be somewhat higher, preferably in the range of 1 to 3 times the film thickness. After the pressing by the door 293 of the blood treatment apparatus 5000, a higher pressing is locally built up (with the effect of the valve tightness) between film 3 and film valve sealing seat edge 226 and the excessive elastomer material of the actuator-sensor-mat 291 softly spreads into the right and left areas of the sealing seat edge through shearing movements. By surface contact of the actuator-sensor-mat 291 on the actuator-sensor-plate 290, the elevation of the buckling or the hump 297 is moderately selected such that the elastical flexibility of the actuator-sensor-mat 291 is sufficient enough to effect a complete form adaptation during uniform pressing along the dented sealing seat edge. This is in particular effected, when one considers the manufacturing precision of the actuator-sensor-mat 291 and possible geometrical changes caused by wear and relaxation.

Devices which increase the flexibility of the actuator-sensor-plate 290 and/or the actuator-sensor-mat 291 are also considered as buckling or hump 297. For this purpose, spring systems are considered, amongst others.

List of Reference Numerals

| Reference Numeral | Description |
| --- | --- |
| 1000 | cassette |
| 1 | hard part |
| 3 | film |
| 4 | sealing bar |
| 5 | closed or peripheral weld |
| 9 | arterial pressure measurement chamber |
| 11 | connector for the exit of blood from cassette 1000 |
| 13 | connector for the entry of blood into cassette 1000 |
| 15 | chamber with arterial post-pump, or pre-filter, pressure measurement site |
| 17 | arterial filter conduit |
| 19 | venous filter conduit |
| 21 | venous blood chamber |
| 23 | upper space of the venous blood chamber 21 |
| 25 | lower space of the venous blood chamber 21 |
| 27 | cross-sectional restriction of the hard part 1 |
| 29 | clot trap |
| 31 | venous patient connection |

-continued

List of Reference Numerals

| Reference Numeral | Description |
|---|---|
| 33 | arterial heparin addition site |
| 35 | check valve of arterial addition site 33 |
| 36 | arterial heparin addition valve (phantom valve) |
| 37 | venous heparin addition site |
| 39 | check valve of the venous heparin addition site |
| 40 | venous heparin addition valve (phantom valve) |
| 41 | substituate addition site |
| 43 | connector for exit of substituate from the cassette 1000 |
| 45 | connector 45 for entry of substituate into the cassette 1000 |
| 47 | check valve for addition of substituate |
| 49 | substituate conduit |
| 51 | pre-dilution addition valve (phantom valve) |
| 53 | post-dilution addition valve (phantom valve) |
| 55 | single-needle sterile membrane |
| 57 | single-needle chamber |
| 59 | blood surge redirection element |
| 61 | single-needle blood valve (phantom valve) |
| 63 | evacuation site for vacuum coupling |
| 65 | primary alignment centre |
| 67 | secondary alignment site |
| 69 | sealing bar |
| 71 | single-needle air connector |
| 73 | support bars having a height of 5 mm |
| 75 | support bars having a height of 8 mm |
| 77 | support bars having a height of 13 mm |
| 79 | support bars having a height of 24 mm |
| 81 | support bars having a height of 31 mm |
| 87 | blood pump |
| 89 | substituate pump |
| 90 | pump tube segment of substituate pump 89 |
| 93 | venous portion of extracorporeal circuit |
| 103 | venous needle |
| 105 | blood inlet at the dialyzing device 2000 |
| 107 | blood outlet from the dialyzing device 2000 |
| 109 | single- needle access to patient 4000 |
| 201 | channel |
| 202 | chamber |
| 204 | closed, flat channel edge bars |
| 226 | section or film sealing seat- bar or valve seat or valve base |
| 288 | phantom or film valve |
| 290 | actuator-sensor-plate |
| 291 | actuator-sensor-mat |
| 293 | door |
| 295 | dent or notch |
| 297 | hump or elevation |
| 301 | hump |
| 303 | main extension plane |
| 305 | split |
| 5000 | blood treatment apparatus |

The invention claimed is:

1. A blood treatment cassette comprising a cassette body having a hard part and a film, wherein the film is connected with the hard part and at least partially covers the hard part,
wherein the hard part comprises a valve base that cooperates with a section of the film adjacent the valve base to form a valve, wherein the valve is configured to be moved from a first open position in which the valve base and the section of the film adjacent the valve base do not touch each other to a second closed position in which the valve base and the section of the film adjacent the valve base touch each other when a force is applied to the section of the film adjacent the valve base,
wherein the hard part and the film are connected to each other along surfaces of channel bars of the hard part that extend alongside chambers or channels of the hard part, wherein the surfaces of the channel bars to which the film are attached define a main contact plane,
wherein the blood treatment cassette comprises, in the area of the valve, at least one hump which is integrally formed with the hard part and which projects through and beyond the main contact plane, and
wherein the hump locally displaces a portion of the film lying above the hump away from the main contact plane so as to sustain the valve in the first open position: (i) while the blood treatment cassette is in a non-use condition and (ii) while the blood treatment cassette is subjected to negative pressures applied within the blood treatment cassette during a sterilization process of the blood treatment cassette.

2. The blood treatment cassette according to claim 1, wherein the valve is configured to be moved from the first position into the second position by pressure applied to the section of the film by an actuator of a blood treatment apparatus when the blood treatment cassette is connected to the blood treatment apparatus.

3. The blood treatment cassette according to claim 1, wherein the valve is a film valve or phantom valve.

4. The blood treatment cassette according to claim 1, wherein a space that is 6 to 12 times the thickness of the film is provided between the valve base and a next adjacent section of the hump in a plane parallel to the main contact plane.

5. The blood treatment cassette according to claim 1, wherein a section of the hump has a diameter that is 5 to 12 times the thickness of the film.

6. The blood treatment cassette according to claim 1, wherein the hump is not part of the channel bars that extend alongside the chambers or the channels of the hard part.

7. The blood treatment cassette according to claim 1, wherein a space that is to 3 to 8 times the diameter of the hump is provided between the hump and an adjacent one of the channel bars in an area where the hump touches the film.

8. The blood treatment cassette according to claim 1, wherein the valve base is arranged at a level of the main contact plane of the film.

9. The blood treatment cassette according to claim 1, wherein the valve base is configured in a flat manner in a longitudinal direction.

10. The blood treatment cassette according to claim 1, wherein the valve base is configured in a curved manner in a longitudinal direction.

11. The blood treatment cassette according to claim 10, wherein the valve base defines a recess having a depth of 2 to 4 times the thickness of the film.

12. The blood treatment cassette according to claim 1, wherein the valve base is configured in a concave manner in a longitudinal direction.

13. The blood treatment cassette according to claim 1, wherein the valve base has a length that is 10 to 30 times the thickness of the film.

14. The blood treatment cassette according to claim 1, wherein the valve base defines a recess having a depth that is 1 to 3 times the thickness of the film.

15. The blood treatment cassette according to claim 1, wherein the valve base is spaced from adjacent channel edge bars by a distance 1 to 3 times the thickness of the film towards the cassette interior.

16. The blood treatment cassette according to claim 1, wherein the hump projects above the valve base by a distance of 2 to 4 times of the thickness of the film.

* * * * *